United States Patent [19]
Millot

[11] Patent Number: 6,167,302
[45] Date of Patent: Dec. 26, 2000

[54] DEVICE FOR TRANSCUTANEOUS ADMINISTRATION OF MEDICATIONS USING IONTOPHORESIS

[75] Inventor: Philippe Millot, Orgeux, France

[73] Assignee: Iomed, Inc., Salt Lake City, Utah

[21] Appl. No.: 09/171,234

[22] PCT Filed: Apr. 15, 1997

[86] PCT No.: PCT/FR97/00672

§ 371 Date: Oct. 15, 1998

§ 102(e) Date: Oct. 15, 1998

[87] PCT Pub. No.: WO97/38750

PCT Pub. Date: Oct. 23, 1997

[30] Foreign Application Priority Data

Apr. 16, 1996 [FR] France ................................ 96 04735

[51] Int. Cl.[7] .................................................. A61N 1/30
[52] U.S. Cl. ............................................ 604/20; 604/501
[58] Field of Search ...................... 604/20, 501; 607/115, 607/116, 149–152

[56] References Cited

U.S. PATENT DOCUMENTS

| 4,931,046 | 6/1990 | Newman ................................... 604/20 |
| 5,591,123 | 1/1997 | Sibalis et al. ............................. 604/20 |
| 5,603,693 | 2/1997 | Frenkel et al. ............................ 604/20 |
| 5,876,368 | 3/1999 | Flower ..................................... 604/20 |
| 5,899,875 | 5/1999 | Millot et al. .............................. 604/20 |

*Primary Examiner*—Glenn K. Dawson
*Assistant Examiner*—Jennifer Maynard
*Attorney, Agent, or Firm*—Factor & Partners, LLC

[57] ABSTRACT

A device for transdermal administration of medication includes a medication reservoir, a set of electrodes made up of an electrode attached to the medication reservoir and a counter electrode, an electronic key loaded with a predetermined code, an electronic module, separably mounted on the set of electrodes, for reading and operating the device according to the predetermined code and for regulating the electric current flowing between the two electrodes and through the reservoir and skin of the patient, and a cradle for holding the electronic module.

15 Claims, 3 Drawing Sheets

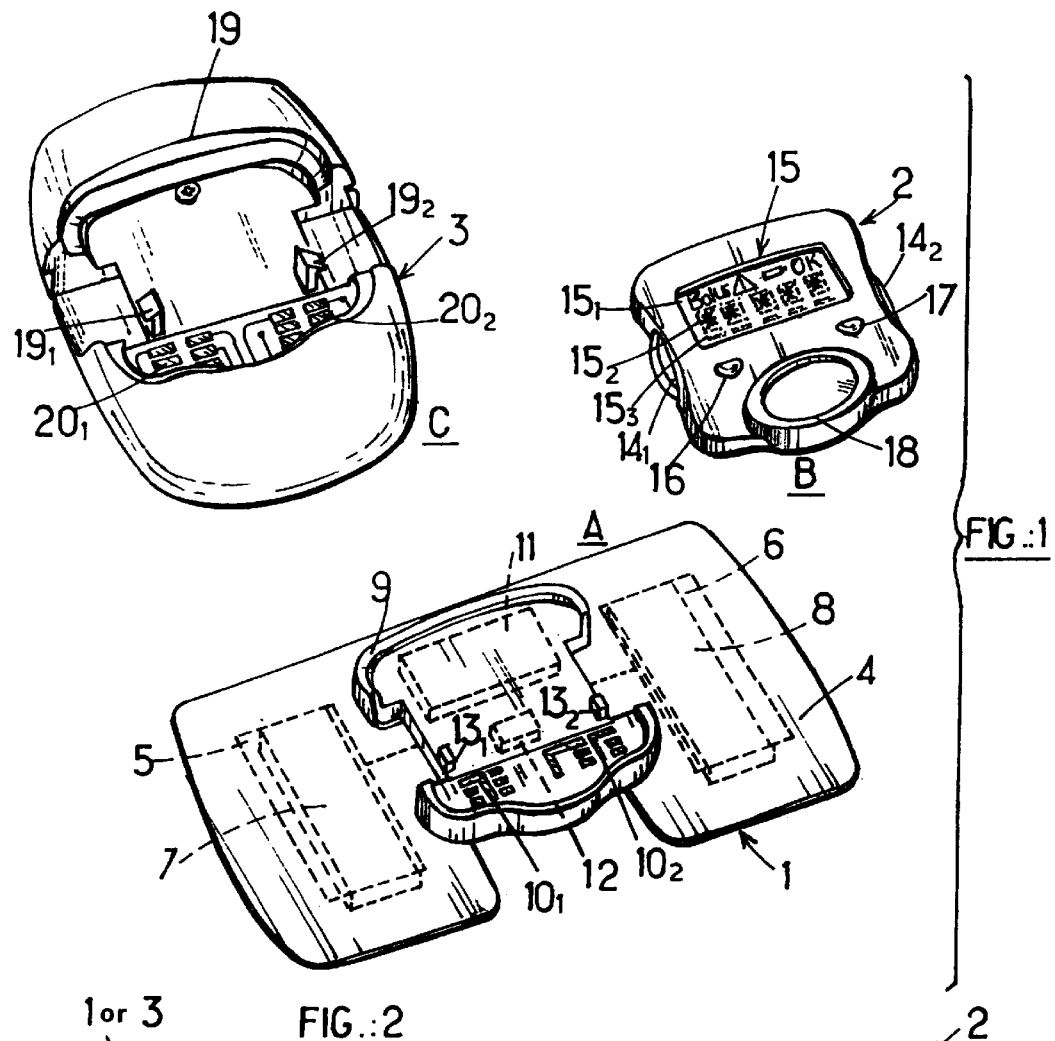
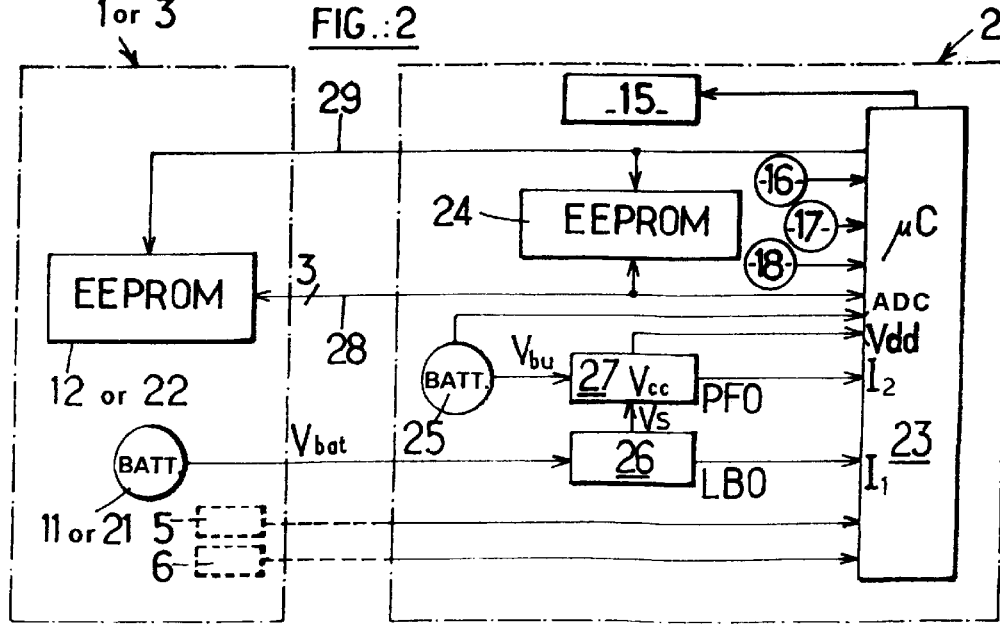

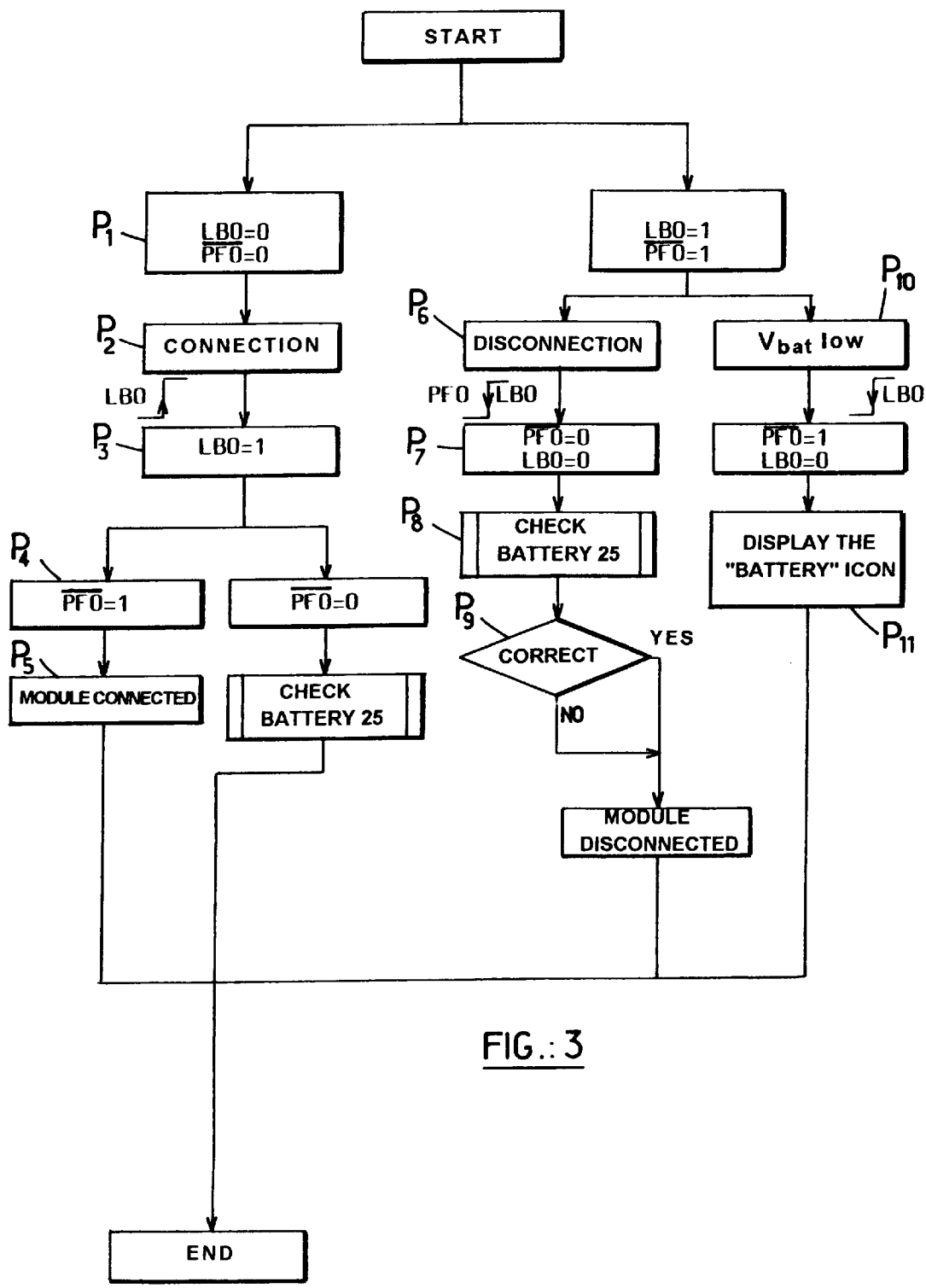
FIG.: 3

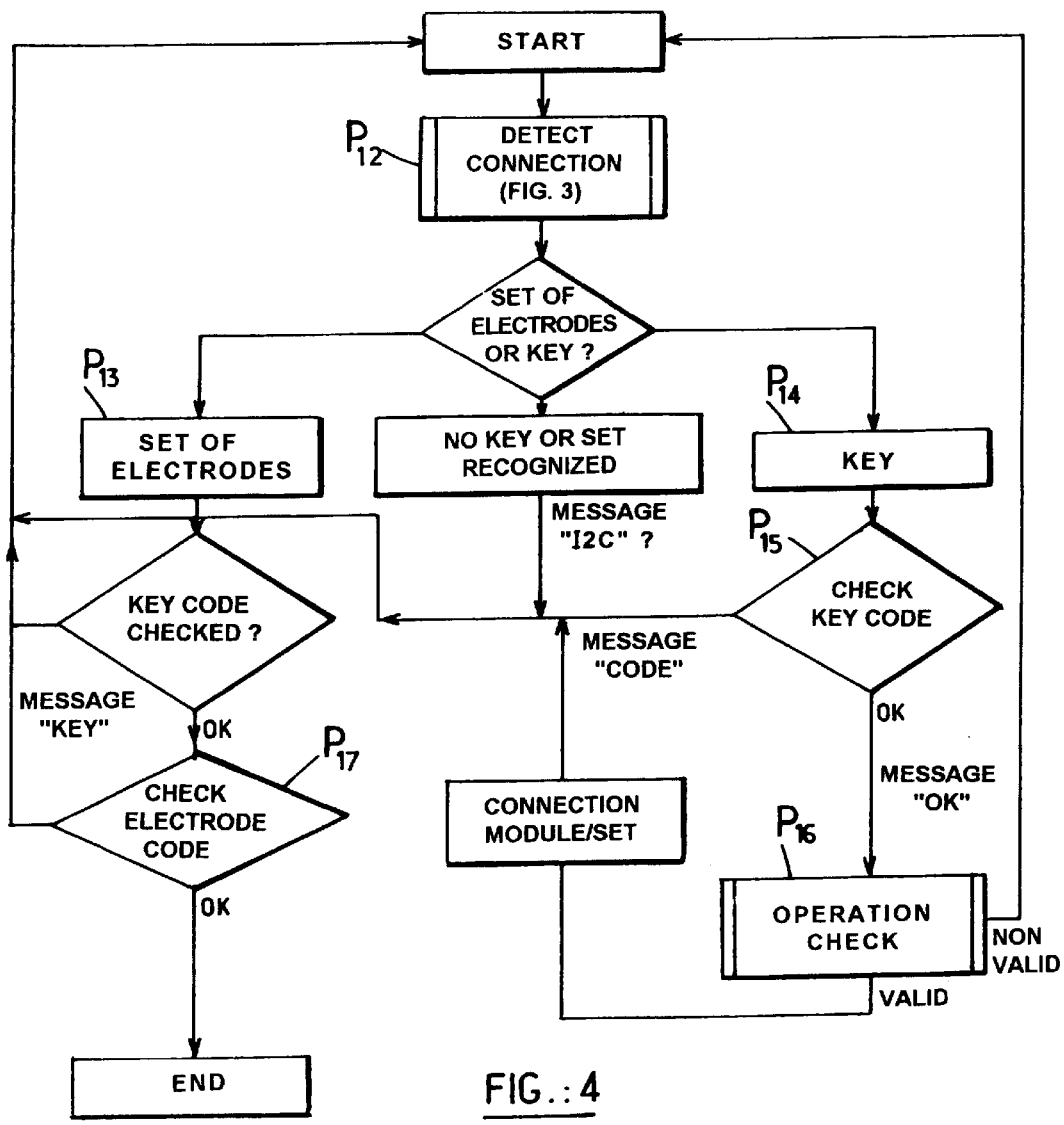
FIG.: 4

DEVICE FOR TRANSCUTANEOUS ADMINISTRATION OF MEDICATIONS USING IONTOPHORESIS

This application is a 371 of International Application PCT/FR97/00672, filed Apr. 15, 1997.

The present invention concerns a device for transdermal administration of medications by iontophoresis and, more particularly, a device of this kind including at least a) a set of electrodes including an electrode joined to a reservoir that can be charged with a medication and a counter-electrode and b) an electronic module that can be separably mounted on said set of electrodes to control the magnitude of an electrical current passing, between the two electrodes, through the reservoir and the skin of a patient pressed against said reservoir.

Devices of the above kind are known in themselves, in particular from international patent applications WO 94/27671, WO 94/28965 and from French patent application no. 2 656 223. They are designed, for example, to administer medication from three therapeutic categories: narcotic analgesics, anti-emetics and anti-migraine medication. The response of patients to narcotic analgesics such as fentanyl and its derivatives, for example, is highly variable. It follows that the treatment must be adapted to suit the patient by the doctor. Iontophoretic devices for administering medication are particularly well suited to this application, because they can execute extremely varied administration programmes that can be modified with great flexibility. All risk of error in the treatment must be avoided, especially in the case of extremely active analgesics such as fentanyl and its derivatives, which can be dangerous, or even fatal, if administered in doses that depart from those precisely determined by pharmacological studies. To this end it is necessary to assure that the medication contained in the reservoir is that chosen and that this medication will be administered in accordance with a controlled programme initiated by a competent person. It is therefore necessary for access to the means for configuring and modifying this programme to be reserved to a competent person to prevent unskilled intervention creating a hazard to the patient.

In this context, the previously mentioned French patent no. 2 656 223 proposes to load into the electronic module all of the medication administration programmes corresponding to the various sets of electrodes that it is able to receive, a particular programme being selected at the time of fitting a particular set of electrodes to the module by mechanical or electrical contact means disposed at the interface between the set and the module to select automatically a programme applicable to the medication contained in the reservoir of the set of electrodes. As an alternative to this, the previously mentioned French patent application proposes that the electronic module should read a bar code carried by the set of electrodes when the two components are assembled together. No means are provided to prevent the use of this device by an unauthorised person.

Furthermore, the use of a bar code restricts the amount of information that can be transferred from the set of electrodes to the electronic module. It necessitates the provision in the module of bar code reading means, which reading can be prevented by interposition of opaque materials in the reading beam. Furthermore, a bar code is readily reproducible by photocopying, which makes potentially dangerous falsifications possible.

The selection of a programme by mechanical means such as projections actuating electrical switches distributed in a particular configuration, or by purely electrical means, has the disadvantage of using fixed configurations of projections or of electrical contacts, which can be readily identified, copied or activated by unauthorised persons.

An aim of the present invention is to provide an iontophoretic device for administering medication designed to assure safe administration both with regard to the competence of the administrator and the selection of the product administered and the administration programme.

Another aim of the invention is to provide a device of the above kind that is nevertheless very versatile in terms of programming and possible reprogramming.

The above aims of the invention, and others that will become apparent from a reading of the following description, are achieved with a device for transdermal administration of medication by iontophoresis comprising at least a) a set of electrodes including an electrode in contact with a reservoir that can be charged with a medication and a counter-electrode, b) an electronic module separably mounted on said set of electrodes to control a therapeutic electric current flowing, between the two electrodes, through the reservoir and the skin of a patient applied against said reservoir, said electronic module comprising means for controlling the operation of the device, characterised in that it further comprises c) an electronic key including a memory loaded with a predetermined code and means for temporary connection to the electronic module to read this code by reading means present in the module, the control means of said module being responsive to the code of said key to authorise selectively the operation of the device.

In a preferred embodiment of the device in accordance with the invention the set of electrodes includes an electronic memory loaded with a predetermined code. The reading means include means for reading said code and said control means also take account of the code from said set of electrodes when selectively authorising the operation of the device.

As will emerge below, the presence of a memory in the set of electrodes enables the storage in the latter of a code identifying the medication contained in the reservoir. This makes reading of this code by the module safer and its decrypting by unauthorised persons more difficult than in the prior art technique referred to hereinabove.

A memory of the above kind is able to store an identification code selected from a virtually unlimited number of such codes, which is advantageous in the context of industrial manufacture. Furthermore, as will become apparent below, this memory is able to receive information other than a code of the above kind, for example an administration programme that can be transferred into the electronic module, which makes a device in accordance with the invention extremely versatile.

Thus administration of medication is enabled only if the administration programme selected is that which corresponds to the medication contained in the set of electrodes and if such administration is required by an approved person, competent doctor or authorised patient. Like the memory of the set of electrodes, that of the key further increases the versatility of the device through the possibility of the latter also receiving administration programmes.

Other features and advantages of the present invention will become apparent from a reading of the following description and from an examination of the accompanying drawings, in which:

FIG. 1 shows a set of electrodes A, an electronic module B and an electronic key C that constitute the components of the device in accordance with the invention, FIG. 2 is a functional schematic showing the structure and the operation of these three components, and FIGS. 3 and 4 are flowcharts of programmes of instructions executed by the electronic module in accordance with the invention.

The latter essentially comprises three separate components, a set of electrodes 1, an electronic module 2 and an electronic "key" 3 respectively shown at A, B, C in FIG. 1.

The set of electrodes 1 includes a flexible film 4, for example of plastics material, having on its face that cannot be seen in FIG. 1, A, two metal electrodes 5 and 6 in contact with respective reservoirs 7, 8 consisting of a layer of a hydrogel, for example. At least one of the reservoirs is designed to receive ionized molecules of an active principle in solution.

During administration of this active principle to a patient, the two electrodes are pressed onto the skin of the patient by means such as a bracelet. The electronic module 2 is then received in a shaped cradle 9 fixed to the other face of the film 4. The module then controls the establishing of an electrical voltage between the electrodes 5 and 6 so that the active principle molecules are forced under the skin of the patient by the electric field established between the two electrodes, as is well known in itself in the field of transdermal administration of medication by iontophoresis.

The necessary electrical connections between the electrical module 2 and the set of electrodes 1 are established by sets of complementary electrical contacts on these two components which are closed when the module is fitted to the cradle 9 of the set of electrodes 1, the contacts $10_1$, $10_2$ carried by the latter being visible inside this cradle. The bottom of the cradle 9 further receives, on the side facing the film 4, an electric battery 11 and an electronic memory chip 12, the function of which is explained below.

The cradle 9 further includes snap fastener teeth $13_1$, $13_2$ which cooperate with flexible tabs $14_1$, $14_2$ formed on the module 2 (see FIG. 1, B) to fasten the module mechanically to its receiving cradle on the set of electrodes 1, pressure applied to the tabs $14_1$, $14_2$ enabling separation of the module from the cradle.

The external view of FIG. 1, B shows that the module 2 further includes a display screen 15 of the liquid crystal type, for example, and pushbuttons 16, 17, 18.

The screen 15 displays icons and messages on three superposed lines $15_1$, $15_2$, $15_3$.

Pressing the pushbutton 16 causes a message "INFO" to appear on line $15_3$. This button is pressed to display information contained in the module 2, such as the time, the dose of medication to be administered, for example in milligrams/hour. This information is displayed on line $15_2$, which includes a row of areas for displaying alphanumeric characters. This line, which can accommodate five alphanumeric characters, for example, is also used to display other messages such as a process initialization message, an error code, etc.

Pressing the pushbutton 17 causes a message "PROGRAMME" to appear in line $15_3$. The doctor presses this button to enter or to modify medication administration programmes, when authorised to do so by the procedures described below.

The patient can press the pushbutton 18 during treatment. This commands the administration of an additional dose (or "bolus") of medication, for example if the patient wishes to alleviate quickly a sharp pain arriving suddenly. When a bolus is requested in this way, a message "BOLUS" appears on line $15_1$ of the screen 15. This line can also display icons to alert the patient or the doctor to the occurrence of a dangerous situation or to a malfunction of the electrical battery power supply of the module, of the set of electrodes or of the key. It can also display a message "OK" to indicate that a treatment can begin, or other useful messages or icons.

As mentioned above, one aim of the present invention is to make transdermal administration of medication by iontophoresis as safe as possible, in the face of possible errors in the nature of the medication administered or in the programme for administering this medication, especially when errors can be dangerous or fatal for the patient. To this end, the device of the invention authorises the administration of a treatment only after execution of a mutual recognition procedure, at least between the set of electrodes and the electronic module, which procedure is described in the remainder of the present description.

To make the administration of the medication even safer, where this is desirable or necessary, the present invention also makes provision for verifying that the treatment was prescribed by a competent person authorised by virtue of holding the electronic key 3. In this case, the device of the invention executes a procedure for mutual recognition of these three components prior to administration of the medication. Administration can then begin only if it is authorised by this procedure, described below with reference to the flowcharts of FIGS. 3 and 4.

Executing this procedure requires that the electronic module is connected in succession to the key 3 and to the set of electrodes 1. To this end, the key 3 includes a cradle 19 with a bottom conforming to that of the module 2, this cradle 19 being provided, like the cradle 9 of the system 1, with two sets of electrical contacts $20_1$, $20_2$, for electrically connecting the key and the module.

Like the set of electrodes 1, the key 3 further includes a battery electrical power supply 21 and an electronic memory 22 that are not shown in FIG. 1, C but which are schematised in FIG. 2, like all the other electrical and electronic means of the device of the invention necessary to execution of the procedure for mutual recognition of the three components of the device.

FIG. 2 schematises the connection of the electronic module 2 to either the set of electrodes 1 or the key 3. Thus the block schematising one of the these components 1 and 3 includes a battery power supply 11 or 21 and a memory 12 or 22, according to whether it is the set of electrodes 1 or the key 3.

The electronic module 2 essentially comprises a process controller 23, usually called a "microcontroller", an electronic memory 24 and a battery 25 providing a back-up power supply to the module, delivering a "back-up" voltage $V_{bu}$ to means (26, 27) for controlling the supply of electrical energy to the microcontroller 23. Incidentally, the microcontroller 23 also controls the display 15, either directly or indirectly.

Moreover, a communication bus 28 enables the microcontroller 23 to read and/or write the various memories 12, 22, 24 of the device of the invention. These memories can be of the EEPROM type, for example, communications being effected via the bus 28 which can be an 12C three-wire synchronous bidirectional master-slave bus, for example. The various memories are then activated by means of an activation line 29 controlled by the microcontroller 23.

In accordance with the invention, the control means (26, 27) are connected both to the backup power supply battery 25 of the microcontroller 23 and to the battery 11 or 21 in the set of electrodes 1 or the key 3, when one or the other of these components is connected to the module 2. In the absence of any such connection, the microcontroller and in particular its internal random access memory are supplied with power by the battery 25 to prevent loss of the data contained in this memory. On the other hand, in accordance with the invention, when this connection is made, the module is advantageously supplied with power by the battery 11 or 21 of the component to which it is connected, so as to spare its back-up battery 25, at least when the voltage delivered by the battery 11 or 21 is sufficient to supply a suitable power supply voltage $V_{dd}$ to the microcontroller. The function of the means (26, 27) is to select and to monitor the batteries that provide this power supply.

To this end, in accordance with one embodiment of the invention given purely by way of example, the power supply control means (26, 27) comprise two integrated circuits available off-the-shelf, respectively a linear regulator 26 and a supervisor 27, respectively listed as MAX 884 and MAX 690 in the catalogues of MAXIM INTEGRATED PRODUCTS of Sunnyvale, Calif., USA.

The regulator 26 has a digital output pin LBO which is high when the regulator is energised, i.e. when it receives a sufficient voltage from the battery 11 or 21 of the component 1 or 3 of the device, respectively, which is connected to the module 2. The signal LBO is applied to an interrupt input $I_1$ of the microcontroller 23 to advise the latter either of correct connection of the battery 11 or 21 supplying a voltage $V_{bat}$ greater than the minimal power supply voltage (for example 4.5 volts) of the regulator 26 (LBO=1) or of disconnection or of an insufficient power supply voltage $V_{bat}$ ($V_{bat}$<4.5 volts), in which situations LBO=0. When LBO=1, the regulator 26 supplies a stabilised voltage $V_s$ of 3.3 volts to the supervisor 27. To this end a divider bridge (not shown) external to the regulator 26 is supplied with the voltage +$V_{bat}$ delivered by the battery. The division ratio of the bridge is chosen so that a voltage +$V_{bat}$=4.5 volts produces a bridge output voltage equal to 1.2 volts. This voltage is fed to a comparator internal to the regulator, the other pin of which receives an internal reference voltage of 1.2 volts. The output of this comparator constitutes the signal LBO.

The supervisor 27 is supplied with power by the battery 25 which supplies to it a nominal voltage $V_{bu}$ of 3 volts. The function of the supervisor is to select either the voltage $V_s$ delivered by the regulator if the latter is present and sufficient or the voltage $V_{bu}$ otherwise as the power supply to the microcontroller 23 which has to receive a voltage $V_{dd}$ at least equal to 2.4 volts. The supervisor 27 has an output pin $\overline{PFO}$ which is high when the voltage $V_s$ delivered by the regulator is greater than 2.4 volts and $V_{bu}$ is greater than 2 volts. The output $\overline{PFO}$ is connected to another interrupt input $I_2$ of the microcontroller 23. When $V_{bu}$<2 V and 2.4 V<$V_{bat}$<4.5 V, $\overline{PFO}$ and LBO are both low. The microcontroller 23 knows (via the bus 28) whether the module 2 is connected to the set of electrodes 1 or to the key 3 or not, but cannot determine if the state $\overline{PFO}$=LBO=0 is because $V_{bu}$<2 volts or because 2.4 volts<$V_{bat}$<4.5 volts. To resolve this ambiguity, the microcontroller 23 is programmed to react to $\overline{PFO}$=LBO=0 by measuring the voltage $V_{bu}$ delivered by the battery via the input ADC of an analogue-digital converter incorporated in the microprocessor. If the measurement indicates $V_{bu}$<2 volts, the microcontroller 23 commands the display of a message on the screen 15 to indicate that the battery 25 must be changed. If $V_{bu}$ is greater than 2 volts, this indicates that the voltage $V_{bat}$ delivered by the battery 11 or 21 is such that 2.4 V<$V_{bat}$<4.5 V. The microcontroller then commands the display of a message inviting the user to replace the battery.

Accordingly the means (26, 27) enable the microcontroller 23 to tell at all times if the module 2 that contains it is electrically or mechanically connected to an external component (key 3 or set of electrodes 1) or not, without being able to tell which of them. The device of the invention uses this capability in the process of mutual recognition of its three components: module, set of electrodes, key, this process being illustrated by the flowcharts of FIGS. 3 and 4 to be described in detail below.

First it is necessary to complete the above description of the device of the invention with reference to FIG. 2. In this connection, it should be remembered that, when the module 2 is mounted on the set of electrodes 1, there is an electrical connection between the module 2 and the electrodes 5 and 6 of the system 1. Because the module 2 controls the electric current flowing between the two electrodes 5 and 6, it needs to measure the voltage between the electrodes to regulate the current to the value it has determined.

The procedure for mutual recognition of the various components of the device of the invention will now be described with reference to the programme flowcharts shown in FIGS. 3 and 4, executed by the microcontroller 23, which is duly programmed to this end.

The process is executed when an authorised patient or practitioner, holding the key, and wishing to initiate a treatment, connects the electronic module 2 successively to the key 3 and then to the set of electrodes 1 to start the medication administration programme, if the procedure authorises such administration. The procedure is started automatically on making the key/module and module/electrode connections. The procedure must therefore incorporate a connection recognition phase, illustrated by the FIG. 3 flowchart, which essentially uses the signals LBO and $\overline{PFO}$ defined above and which have the following states:

LBO=1 if $V_{bat}$>4.5 volts

LBO=0 if $V_{bat}$<4.5 volts $\overline{PFO}$=0 if $V_{bat}$<2.4 volts or if $V_{bu}$<2 volts $\overline{PFO}$=1 if $V_{bat}$>2.4 volts and $V_{bu}$>2 volts Before a key/module or module/electrode connection, LBO=$\overline{PFO}$=0 (step $P_1$ of the flowchart). On step $P_2$, the patient or the doctor establishes a connection which can be either a key/module connection or a module/electrode connection. This connection causes LBO to go from 0 to 1 (step $P_3$) if the voltage $V_{bat}$ delivered by the battery 11 or 21 of the set of electrodes 1 or of the key 3 is greater than 4.5 volts. If $V_{bat}$<4.5 volts, LBO remains at 0 and a message indicating the weakness of the battery is displayed on the screen 15, as mentioned above. The sequence starts again before step $P_1$. On step $P_4$, the microcontroller tests $\overline{PFO}$. If $\overline{PFO}$ has gone to 1, the regulator 26 is delivering $V_s$=3.3 volts and $V_{bu}$ is greater than 2 volts. The microprocessor deduces from this that the module is connected to the set of electrodes 1 or to the key 3 without being able to tell which one (step $P_5$). Otherwise ($\overline{PFO}$=0), this means that $V_{bu}$ is lower than 2 volts and that it is necessary to change the spent battery 25 of the module.

On separation of the module and the component (key or set of electrodes) from the device connected to it, it is possible to draw conclusions from how the signals LBO and $\overline{PFO}$ change as to the occurrence of this disconnection and as to the condition of the batteries of the device. Starting from an initial state in which LBO=$\overline{PFO}$=1, signifying a connection with adequate voltages $V_{bat}$ and $V_{bu}$, necessary to start and execute a treatment, this initial state can be modified either by disconnection at the end of treatment, for example (step $P_6$), or by a drop in the voltage $V_{bat}$ supplied during the treatment to the module 2 by the set of electrodes 1 or the key 3 (step $P_7$) below the 4.5 volt threshold. In the case of a disconnection, $\overline{PFO}$=LBO=0 is read in step $P_7$. When $\overline{PFO}$ goes low (step $P_8$), the voltage $V_{bu}$ supplied by the battery 25 is checked via the analogue-digital converter incorporated in the microcontroller 23. Accordingly, in addition to the disconnection information received by the microcontroller when LBO goes low, this test advises whether it is necessary or not to change the back-up battery 25 (step $P_9$). The microcontroller then displays an icon on the screen 25 to report this situation to the patient and/or the doctor.

The battery 11 of the set of electrodes, which supplies the electrical current required for the treatment under the control of the microcontroller, may run down during a treatment started when LBO=$\overline{PFO}$=1, (step $P_{10}$). LBO then goes low. In step $P_{11}$, the microcontroller commands the display of an icon on the screen 15 of the module to tell the patient or the doctor that it is necessary to change the battery 11, as mentioned above.

The method described hereinabove enables the microcontroller 23 of the module 2 to be aware at all times of its state of connection to/disconnection from another component of the device and as to the status of the batteries of the module and this component.

Having detected a connection, the microcontroller 23 of the module 2 can start a procedure for recognising a component of the device (1, 2, 3) that is connected to the module and for verifying the compatibility of this component with the module. To this end, the microcontroller must read and compare the data contained in the three EEPROM 12, 22, 24 of the device. Each memory has a particular address and stores at least one code used by the process for recognizing the compatibility of the components of the device. It can also receive one or more medication administration programmes that can be executed under the control of the microcontroller. This is the case in particular of the memories 12 and 24 of the set of electrodes 1 and the module 2. The memory 22 of the key can also receive a programme of this kind, as will emerge below.

An address on two bits $E_1E_2$ is sufficient to enable the microcontroller 23 to access these three memories selectively and to identify the component (set of electrodes/key) to which it is connected. Addressing on two bits can accommodate a fourth memory in one or other of the components of the device to hold data useful for the processing carried out by the device of the invention.

Each of the memories 12 and 22 of the set of electrodes 1 and of the key 3, respectively, also contains a respective identification code C1, C3 specific to the set of electrodes 1 and to the key 3, respectively. The memory 24 of the module 2 contains the identification codes of the key 3 and of the set of electrodes 1 that are compatible with the electronic module 2, from the point of view of the medication contained in the set of electrodes, its administration programme stored in the module and the person (competent doctor or patient) authorized to carry out the treatment.

Accordingly, the device in accordance with the invention assures that the three-fold safety condition that must govern administration is fully complied with where a particular medication must only be administered in accordance with a particular administration programme, under the authority and control of a certain person.

The procedure for verifying this three-fold safety condition in accordance with the invention will now be described with reference to the FIG. 4 flowchart.

The programme for detecting connection/disconnection of components of the device of the invention, described with reference to the FIG. 3 flowchart, being executed continuously by the microcontroller 23, in a few microseconds, the latter knows at all times whether it is connected or not. On detecting a connection (step $P_{12}$, FIG. 4) the microcontroller identifies the connected component by reading in the memory of the latter the address $E_1$ $E_2$ specific to it. If its address indicates that the component connected to the module is the set of electrodes 1 (step $P_{13}$), the programme looks to see if the key 3 has been previously connected to the module (in the case of a process involving this key) and recognised as compatible by the latter. If not, during the preparation of a treatment the keyholder has not inserted the module in their key. The microcontroller 23 then commands the display on the screen 15 of the module 2 of a message "key" to advise the keyholder that they must first of all insert the module 2 in their key. The cycle described above continues until this is done (step $P_{14}$).

The microcontroller then checks (step $P_{15}$) the code C3 contained in the memory 22 of the key 3. If the latter is recognised or accepted by the module 2, the display screen 15 of the latter shows a message "OK" to advise the keyholder 3 that they are authorised to use the device of the invention, at least with sets of electrodes charged with certain medications.

In one particular embodiment of the invention, if the code C3 of the key is accepted by the module 2, a subroutine verifies correct operation of the device in the medication administration phase, in particular its capacity to command the magnitude of the "therapeutic" current. To this end the key advantageously contains an impedance Z simulating that of the skin of a patient. The module 2 then outputs into this impedance (step $P_{16}$) a current measured by the microcontroller 23. The measured value is compared with values stored in memory. If the comparison indicates that the module is operating correctly, the sequence to verify the code C1 from the set of electrodes 1 may begin, as soon as the module is withdrawn from the key 3 and installed in the set of electrodes (step $P_{17}$). If, on the other hand, the module rejects the key, the keyholder is advised by the appearance of a message "code" on the screen 15. The verification cycle begins again, until a key is accepted by the module.

If the code C1 of the set of electrodes 1 mounted on the module is not recognised by the latter, the holder of the set of electrodes is advised by the display of a message "code" on the screen 15. If, on the other hand, this code is recognised by the microcontroller, a message "OK" appears on the screen to indicate that treatment may begin.

It is now apparent that, by using the device of the invention, the patient is perfectly safe in the situation in which the treatment requires precautions to be taken as to the capacity of the administrator to apply this treatment, the nature of the medication administered and whether the programme for administration of this medication is adequate, as commanded by the electronic module. It will further be noted that the device of the invention also includes means for verifying correct operation of the electronic module before starting treatment and with the batteries in a good state of charge, both before and after treatment.

Of course, the invention is not limited to the embodiment described and shown which has been given by way of example only. Accordingly, the medication administration programme can initially be recorded elsewhere than in the electronic module, that is to say either in the memory of the key or in the memory of the set of electrodes. When the administration programme is initially stored in the key, treatment can begin as soon as the module is mounted on a set of electrodes after unlocking the module with the key.

The administration programme can also be stored initially in the memory 12 of the set of electrodes 1, which thus takes on board the programme associated with the medication that it contains. The module reads the programme stored in the memory 12 of the set of electrodes 1 and executes it. This enables different preprogramming of the sets of electrodes of a plurality of such sets before they are used in succession, for example to administer doses of medication to the patient increasing or decreasing day by day.

The administration programme can be initially stored in the memory 22 of the key 3. In this case it must be copied into the memory 24 of the module 2 when the latter is mounted on the key during the recognition phase. The treatment is then controlled entirely by the person holding the key, a doctor or a pharmacist, for example. After this person charges loading the set of electrodes, the system can be used by the patient.

The electronic module of the device in accordance with the invention has been described hereinabove as containing the code of only one key and that of only one set of electrodes, in order to simplify the description of how it works. As an alternative to this, however, the memory of the module could contain the codes of several keys to authorise several equally qualified persons to initiate a treatment. An alternative solution is to allocate the same key code to several qualified persons on the staff of the same nursing centre, for example.

Likewise, the electronic module 2 can store in memory several codes of sets of electrodes, for example if the same treatment entails the use of a batch of sets of electrodes, used successively, the sets of one batch being charged with different medications that complement one another for a particular treatment.

When a treatment does not require supervision by a person of particular competence, because of the absence of danger, for example, the mutual recognition of the components of the device in accordance with the invention involves only the code of the set of electrodes, the module being duly programmed to eliminate the process of recognition of the key.

Likewise, when the treatment does not require checking of the compatibility of the set of electrodes with the electronic module employed, because the administration device can receive only one type of electrode, for example, the mutual recognition of the components of the device involves only the key and the electronic module.

All of the foregoing description relates to the invention in its application to transdermal administration of medication under the influence of an ionophoretic force. It is nevertheless clear that the invention can also find applications in the trandermal administration of medication by electro-osmosis.

What is claimed is:

1. Device for transdermal administration of medication by iontophoresis or electro-osmosis comprising at least a) a set of electrodes (1) including an electrode (5) joined to a reservoir (7) that can be charged with a medication and a counter-electrode (6), b) an electronic module (2) separably mounted on said set of electrodes (1) to control a therapeutic electric current flowing, between the two electrodes (5,6), through the reservoir (7) and the skin of a patient applied against said reservoir, said electronic module (2) comprising means (23) for controlling the operation of the device, said device further comprising c) an electronic key (3) including a memory (22) loaded with a predetermined code (C3), a cradle (19) to temporarily receive said module and means (20$_1$, 20$_2$) for establishing electrical connections to said module (2) to read this code (C3) by reading means (28) present in the module, said control means (23) of said module being responsive to the code (C3) of said key to authorise selectively the operation of the device.

2. Device according to claim 1, wherein the set of electrodes (1) includes an electronic memory (12) loaded with a predetermined code (C1), in that said means (28) include means for reading said code (C1) and in that said control means (23) also take into account the code (C1) of said set (1) to selectively authorize the operation of the device.

3. Device according to claim 1 wherein the set of electrodes (1) includes a cradle (9) receiving the module (2) and means (10$_1$, 10$_2$) for making electrical connections to this module.

4. Device according to claim 1 wherein the set of electrodes (1) and the key (3) each include mechanical connection means (13$_1$, 13$_2$; 19$_1$, 19$_2$) cooperating with mechanical means (14$_1$, 14$_2$) of the module to connect them temporarily to this module.

5. Device according to claim 1 wherein the set of electrodes (1) includes an electrical power supply battery (11) and means for supplying electrical energy to the module (2) from the battery (11) when they are connected.

6. Device according to claim 1 wherein the key (3) includes an electrical power supply battery (21) and means for supplying electrical power to the module (2) from the battery (21) when they are connected.

7. Device according to claim 1 wherein said means for controlling the operation of the device comprise a microcontroller (23) and an associated electronic memory (24) in the module, said memory (24) being loaded with the codes (C1; C3) of at least one set of electrodes (1) and of at least one key (3) forming part of the device, said microcontroller being programmed to read the code contained in the memory (22) of a key (3) and the code contained in the memory of said set of electrodes (1), respectively, to compare them with the corresponding codes stored in its own memory (24) and to authorize administration of the medication when the codes (C1; C3) of said key and of said set of electrodes are identical to the corresponding codes stored in its own memory (24).

8. Device according to claim 7 wherein the module (2) includes means (26, 27) for controlling the supply of electrical energy to the microcontroller (23), these means including a regulator (26) supplied with energy by a battery (11; 21) of the key (3) or of the set of electrodes (1) when one or other supplying these components is connected to the module (2), and a supervisor circuit (27) supplied with energy by a back-up electrical power supply battery (25) adapted to supply energy to the module when it is not supplied with energy by a battery (11; 21) of the key (3) or of the set of electrodes (1), respectively, the supervisor circuit (27) selectively controlling the supply of energy to the microcontroller (23) either from the output of the regulator (26) or from said back-up battery (25).

9. Device according to claim 8 wherein the microcontroller receives a digital signal (LBO) from the regulator (26) indicating whether the regulator is supplied with electrical energy or not and a digital signal (PFO) from the supervisor circuit (27) and indicating whether a voltage (Vs) supplied by the regulator (26) to said circuit (27) is above a predetermined threshold while the voltage supplied to said circuit (C7) by the battery (25) of the module is also above a predetermined threshold or that these two voltages are below the corresponding thresholds, the microcontroller being programmed to deduce from the logical levels of the signals (LBO, PFO) whether the module (2) is connected to or disconnected from either of the components (1) and (3) of the device.

10. Device according to claim 9 wherein the microcontroller (23) is also programmed to derive from the logic levels of the signals (LBO, $\overline{\text{PFO}}$) information as to a condition of the back-up power supply battery (25) of the microcontroller (23) and a condition of the battery (11 or 21) of a component (1 or 3) if connected to the module (2).

11. Device according to claim 9 wherein the electronic module (2) includes a screen (15) for displaying messages and icons, this screen being controlled to display messages and information established by the microcontroller (23) during execution of the programmes for which it is responsible.

12. Device according to claim 11 wherein microcontroller (23) is programmed, following detection of a module (2)/key (3) or module (2)/electrode (1) connection, to a) send an alert message ("key") to the screen (15) when a module (2)/electrode (1) connection is present with no prior module (2)/key (3) connection, b) compare the code (C3) in the memory (22) of the key (3) to the corresponding code placed in the memory (24) of the module (2) upon first connection of the module (2) to the key (3), c) prohibit treatment if the codes compared are not identical, d) compare the code (C1) in the memory (12) of the set of electrodes (1) to the corresponding code in the memory (24) of the module (2) upon subsequent connection of the set of electrodes and the module, if the treatment is not prohibited, and e) enabling the treatment if the latter codes are identical.

13. Device according to claim 12 wherein it includes a subroutine for verifying the operation of a programme for controlling the therapeutic current flowing between the electrodes (5, 6) of the set of electrodes (1) during execution of the treatment, execution of this subroutine being initiated by recognition of the code of the key (3) of the module (2), an electrical impedance (Z) being mounted in the key (3) to be energised by an electrical current commanded by the module (2) to stimulate the skin during the execution of said subroutine.

14. Device according to claim 1 including means (12; 22; 24) for storing in memory a programme for controlling the therapeutic current, wherein said means for storage in memory are located in any one of the three components (1, 2, 3) of the device.

15. Device according to claim 14 wherein said means for storage in memory (22) are in the key (3), further comprising (23) for controlling the transfer of the programme contained in the memory (22) of the key (3) into the memory (24) of the electronic module (2) upon key (3)/module (2) connection.

* * * * *